United States Patent [19]

Saltarelli

[11] 4,182,753

[45] Jan. 8, 1980

[54] SARCOMA 180 TUMOR INHIBITOR AND METHOD OF MAKING SAME

[76] Inventor: Cora G. Saltarelli, 2323 Areca Rd., Boca Raton, Fla. 33432

[21] Appl. No.: 891,334

[22] Filed: Mar. 29, 1978

[51] Int. Cl.$^2$ ............................................ A61K 35/00
[52] U.S. Cl. ..................................... 424/115; 424/95;
424/181; 435/922; 435/68
[58] Field of Search ......................... 424/95, 115, 181;
195/81

[56] References Cited
PUBLICATIONS

Suzuki et al., Gann, 60: 65–69, Feb. 1969.

*Primary Examiner*—Jerome D. Goldberg
*Attorney, Agent, or Firm*—Hill, Van Santen, Steadman, Chiara & Simpson

[57] ABSTRACT

A Sarcoma 180 tumor growth inhibiting glycoprotein material produced extracellularly from *Candida albicans* is provided. The inhibitor material is effective to arrest Sarcoma 180 tumor angiogenesis thereby causing tumor regression. The preferred inhibitor material is an extracellular glycoprotein produced from *Candida albicans* SA#1 (CBS 5736) cultured in a glucose containing chemical medium with a filtrate of the growth medium precipitated with ethanol. Dosage innoculations of the precipitate into the peritoneal cavities of Sarcoma 180 tumor infected mice effect substantial tumor regression.

5 Claims, No Drawings

SARCOMA 180 TUMOR INHIBITOR AND METHOD OF MAKING SAME

FIELD OF THE INVENTION

This invention relates to the art of inhibiting Sarcoma 180 tumor growths in living tissue with materials arresting angiogenesis. Specifically the invention deals with glycoprotein materials produced extracellularly from a strain of *Candida albicans* which is effective to inhibit the growth of solid Sarcoma 180 tumors. The invention includes the method of making the glycoprotein material.

BACKGROUND OF THE INVENTION

It is known that solid tumors cannot grow unless they are vascularized and when the blood supply to such tumors is arrested, tumor regression will soon follow.

The present invention provides an antitumor effect on solid Sarcoma 180 tumors in living tissue by arresting the blood supply to the tumor without adverse side effects such as ulcerations, hemorrhaging, or necrosis which might be expected in any attack on a vascular system.

SUMMARY OF THIS INVENTION

This invention provides a Sarcoma 180 tumor inhibitor or antitumor composition which inhibits the growth of blood vessels supporting the tumor and probably develops an antibody-antigen reaction producing substantial tumor regression. Th inhibitor of the invention is an extracellular glycoprotein complex produced by *Candida albicans* SA#1 in a chemically defined medium. A glycoprotein complex can be produced from other variants of *Candida albicans* but since some of the precipitates of the polymer were toxic enough to effect the centraL nervous system of the mice, it was found that the *Candida albicans* SA#1 strain was most reliable and the studies were conducted with the SA#1 strain. This material is injected into living tissue surrounding a growing Sarcoma 180 tumor and soon decreases the blood vessels surrounding and feeding the tumor resulting in tumor inhibition as high as 88% with a single treatment and over 90% when administered in multiple dosage units on successive days. The material is immunologically active, nontoxic, and nonallergenic.

A strain of *Candida albicans* (SA#1) (CBS-5736) is a preferred micro-organism producing a high concentration of glycoproteins extracellulary to form the inhibitor of this invention. This strain of *Candida albicans* is cultured in a chemically defined (CD) medium of the following preferred formulation:

$CaCl_2.2H_2O$—0.1 g
NaCl—0.1 g
$MgSO_4.7H_2O$—0.4 g
$K_2HPO_4$—1.0 g
$(NH_4)_2SO_4$—3.5 g
glucose—40.0 g
per liter.

The pH of the medium was adjusted to 5.6 and trace metals $Mn^{++}$, $Zn^{++}$, $Cu^{++}$ and $Fe^{++}$, $22.25 \times 10^{-3}$ ionic strength per milliliter were added. The medium was then autoclaved and biotin in the amount of 12.5 ug per liter of distilled water was added after autoclaving.

The *Candida albicans* strain SA#1, cultured in the above CD medium was incubated for 30 days at 30° C., the growth medium was centrifuged, sterilized by Seitz filtration, and the cells were discarded. The remaining filtrate was precipitated with 95% ethanol (1:5) to yield the glycoprotein fraction. This fraction was evaporated to dry, and the dried precipitate was reconstituted with sterile distilled water (10 mg/ml, pH 7.0).

From the above description, it will be understood that the Sarcoma 180 tumor growth inhibitor is an ethanol precipitate of glycoprotein synthesized from *Candida albicans*. It should be also understood that this glycoprotein material can be cultured in any suitable CD medium containing glucose which will develop polysaccharide-protein complexes from the *Candida albicans* SA#1. The medium is simple and lends itself to easy chemical and physical analysis. Addition of other ingredients or exchanging the glucose with sucrose could produce a different polymer with different biological activities.

It is, therefore, an object of this invention to provide a solid Sarcoma 180 tumor inhibitor glycoprotein composition produced extracellularly from *Candida albicans* microorganisms.

A specific object of the invention is to provide a Sarcoma 180 tumor growth inhibitor composition comprising an ethanol precipitate of glycoprotein material synthesized from *Candida albicans* SA#1 which is effective to attack the vascular system of solid tumors in living tissue.

A further object of the invention is to provide a method of making a solid Sarcoma 180 tumor growth inhibitor from *Candida albicans* SA#1 microorganisms.

Another specific object of the invention is to provide a method of making a polysaccharide-protein from *Candida albicans* effective to attack the vascular system of solid Sarcoma 180 tumors in living tissue.

Other and further objects of this invention will be apparent to those skilled in this art from the following detailed descriptions of experiments conducted on mice using the above-described glycoprotein composition:

TRANSPLANT AND TREATMENT OF TUMORS

Sarcoma 180 is a transplantable tumor of Swiss female mice. The solid tumor was cut into small, uniform pieces weighing approximately 5.0 mg and inoculated subcutaneously by trocar needle (13 gauge, 100 mm long) into the right auxillary region of 6-8 week old Swiss Ha/ICR female mice weighing about 24-25 grams. Sterile instruments and water were employed and antibiotics were not used at any time. After transplant, each group of experimental mice received intraperitoneal injections of varied dosages of 1.0 ml of the above produced *Candida albicans* SA#1 ethanol precipitate in sterile distilled water.

SINGLE AND MULTIPLE TREATMENTS

Two experiments were conducted to ascertain the most effective day of treatment after transplant and also the effectiveness of multiple doses using the same concentration of treatment (10 mg SA#1 precipitate/ml sterile water). Therapy effectiveness was evaluated by the excision and weighing of tumors. The first experiment consisted of seven groups of mice containing approximately ten mice, each receiving a single treatment, three to ten days after tumor transplant. The other experiment consisted of four groups of mice containing approximately ten mice each which received more than one injection after tumor transplant; one group received treatments on days three and four, one on days three through five, another on days three through six, and the last group on days three through seven. The controls received 1.0 ml of either sterile CD medium or saline.

All of the mice in these two experiments were killed nine days after the last treatment; the tumors were excised and kept in a humidity chamber until the wet weights were determined, than air dried 24 hours for dry weight determinations. The average dry wet weights for each experimental ($W_e$) and control group ($W_c$) were used to determine the percent inhibition of the tumors $$(\frac{W_e - W_c}{W_c} \times 100).$$

The average body weight of the mice in each group was determined daily.

Tumor excision was easily performed since the tumor itself was clearly differentiated from surrounding tissue by gross visual appearance. Infected or necrotic tissue surrounding the tumor mass was not found and excess supporting tissue was easily removed without difficulty from the solid enclosed tumor.

The most effective day of treatment was established as the ninth day after transplant and subsequent experiments were carried out to see if treatment was dose dependent, and also to determine if multiple doses given on days 9 and 18 would be more effective in tumor inhibition. Therapy effectiveness was evaluated by mean survival times and also mean tumor diameters (length (mm)×width (mm) which were the final measurements taken on the day before death.

One group of mice (Group 1, 28 mice) received 10 mg of precipitated glycoprotein in 1.0 ml sterile water on day 9; another (Group 2, 34 mice) received 20 mg/ml on day 9; and another (Group 3, 34 mice) received 10 mg/ml on days 9 and 18 after transplant. The control mice (Group 4, 35 mice) did not receive any treatment except 1.0 ml of saline.

All the mice in all of these experiments received the S-180 tumor from the same tumor generation and were randomized into the four experimental groups. The mice were also identified so that daily weights and measurements could be taken and recorded.

Preliminary studies were made to determine the mechanism of tumor inhibition and to study the effect of the therapy on the vascular system. A single dose of 20 mg/ml of the ethanol precipitate was injected (Ip) on the 8th day after transplant and the experimental as well as the control mice were sacrificed at various intravals.

A preliminary study was also made to test the possibility that the antibody-antigen system could inhibit transplantation of the tumors since the therapy stimulated the formation of a high antibody titer within 24–48 hours. A group of 10 mice were given 20 mg/ml of the ethanol precipitate 48 hours before transplanting tumors.

STATISTICAL ANALYSIS

The data was analyzed using Chi-square and the Student's t-test (one tailed test). The median and mean survival times were calculated (13) using day 55 as the evaluation day.

HEMATOLOGY STUDY

In order to determine the effect of the treatment on the hemopoietic system, white cell counts and differentials of twenty individual female Ha/ICR mice, not bearing tumors, were determined before and after injection (i.p.) of the SA#1 ethanol precipitate treatment. On days two to ten, two mice were sacrificed daily by retro-orbital bleeding. The whole blood was used for the hematological study and the serum was frozen for future antibody-antigen tests against the ethanol precipitate material using the ring precipitin test.

IMMUNOLOGICAL ACTIVITY OF THE WHOLE FILTRATE

The immunological activity of the glycoprotein complex in the filtrate was studied by the ring precipitin reaction, microimmunoelectrophoresis, and whole cell agglutination tests using rabbit antiserum developed against the glycoprotein complex. Comparative rates of antibody development and titers were made using as antigens the sonicated yeast cells, the whole filtrate, the ethanol precipitate of the whole filtrate, and the molecular weight fractions of the filtrate.

The sonicated cells had been cultured 48 hours, 30° C., in Sabouraud's dextrose broth, washed three times with sterile water, and disrupted with an ultrasonic probe (Branson Sonifier, Branson Instruments, Inc., Danbury, Conn.).

The molecular weight fractions (MW) consisted of Fraction I, MW less than 1K; Fraction II, MW greater than 1K but less than 10K; and Fraction III, MW greater than 10K (Amicon Ultra-filtration System with Diaflo Membranes, Amicon Corp., Lexington, Mass.).

The rabbit antiserum was prepared by immunizing three albino rabbits each with the whole Seitz filtered filtrate of SA#1 or the sonicated cell suspension. Preliminary sensitivity tests had shown positive reactions within 24 hours. Weekly injections given to the rabbits consisted of 2.0 ml of the antigen mixed with 2.0 ml of Freund's complete adjuvant injected subcutaneously in the neck and intramuscularly into each thigh of the rabbits.

The antibody titer was determined by the ring precipitin reaction in which serial dilutions were made with 0.9% unbuffered NaCL solution and the amount of precipitate (quantitated 1+ to 4+) was determined.

Microimmunoelectrophoresis on glass slides containing 0.025 ionic strength buffered sodium barbitol with 2% Noble agar (final pH 8.2) was performed (14). The antigen was placed in the center well and electrophoresis was maintained for one hour at 65 milliamperes at 10° C. The antiserum was placed in the troughs and diffusion was allowed to take place for 20 hours in a moist sealed container at room temperature. The dried slides were stained with amido schwartz after removal of the excess serum with unbuffered 0.9% NaCl.

The degree of agglutination of *C. albicans* cells by the rabbit antiserum was obtained by serially diluting the antiserum with 0.9% unbuffered NaCl solution and adding an equal amount of cells ($8.6 \times 10^6$ cells/ml unbuffered NaCl) to the serum and quantitating the degree of agglutination (1+ to 4+) with magnification of 10 X.

RESULTS

The chemically defined medium alone was neither toxic, lethal, nor inhibitory to Sarcoma 180 tumors when tested. The tumor bearing group of mice which received chemically defined medium only was not significantly different from the tumors of the control group which received no treatments. Allergic reactions were not observed when the mice were treated with the ethanol precipitate.

Chemical analysis per milliliter of whole filtrate before precipitation yielded: 1.05 mg hexose, 0.0085 mg glucose and 0.665 mg protein. The ethanol precipitate, which was dried and reconstituted with sterile distilled water, contained 0.20 mg hexose, 0.00225 mg glucose and approximately 0.005 mg protein per milliliter. The ethanol precipitate was easily harvested and 2.0 g per liter was recovered from the whole filtrate after 30 days incubation at 30° C.

SINGLE AND MULTIPLE TREATMENT

A substantial weight loss by the experimental groups in the preliminary studies receiving single treatments and multiple treatments after transplant as compared to the control group was observed. However, the greatest decrease of weight of an experimental group occurred when the mice were treated with the ethanol precipitate on the third and fourth days after tumor transplant.

Table 1 presents the average wet and dry Sarcoma 180 tumor weights after single treatments. The greatest tumor inhibition occurred when a single dose was given nine days after tumor transplant (88.0%, $X^2=71$, $p<0.0005$ for wet weight) although substantial and highly significant inhibition occurred on and after the sixth day.

Table 2 lists the average Sarcoma 180 tumor weights obtained from the experimental and control groups of mice after the administration of consecutive multiple treatments from day 3 through day 7. Using chi-square analysis on the wet weight data, all treated groups showed significant decreases in tumor size as compared to the control.

Comparative analysis using wet weight values between single and multiple doses revealed an overall increase in the percent Sarcoma 180 tumor inhibition shown by the groups receiving multiple doses. Therefore, it appeared that multiple treatments resulted in greater tumor inhibition than single treatments. However, maximum inhibition (90.4%) obtained by administering five doses could almost be achieved by giving one treatment (88.0%) on the ninth day after tumor transplant.

The results of subsequent experiments comparing the survival times of animals receiving varied treatments are presented in Table 3. All treated groups as compared to the control had an increased percentage of survivors. The total percentage of survivors in the treated groups at evaluation day (day 55) was 25% and of this 20% were without tumors; the control group had 5.7% survivors of which only 2.8% did not have tumors. There was little difference in the percentage of survivors between the three treated groups. The mice that survived were observed for four months after evaluation day without reappearance of the tumor.

The median survival times, which denote the day of death at which one half of the animals died earlier and the other half survived or died later, are relatively the same for all experimental groups including the control. However, a considerable difference exists in the mean survival times among groups.

Group 1, receiving 10 mg glycoprotein/ml, had a 3.9% increase in survival time; Group 2, which received 20 mg/ml had a 21.7% increase in survival time; and Group 3, which received 10 mg/ml, on days 9 and 18, increased in survival time by 29.6%.

Mean tumor diameters used as an evaluator of in vivo testing indicated a positive treatment effectiveness in all experimental groups. Using the Student's t test, the tumors of all treated groups were significantly smaller than the controls: Group 1, d.f. 63, t=2.46, $P<0.025$; Group 2, d.f. 67, t=2.01, $p<0.025$; Group 3, d.f.=67, t=2.1, $p<0.025$. There was no significant difference between treated groups.

At no time did the Sarcoma 180 tumor-bearing mice or non-tumor-bearing mice treated and tested with the ethanol precipitate show any obvious abnormalities or general side effects such as ulceration, loss of hair, or central nervous system aberrations.

Hematology Study

Variation in blood counts and differentials were within the normal range established for Swiss mice and also within the range of the controls.

The ring precipitin test, in which the pooled serum from two mice (injected with the ethanol precipitate only) was diluted 1:2 and 1:4 times with unbuffered saline, produced the greatest amount of precipitation with the antigen between the 6th and 8th days after the initial injection of the antigen. The amount of precipitate started to increase on the second day, was maximal on the 6th and 7th days, and started to decline on the 8th, 9th, and 10th days.

Immunological Activity of the Filtrate

The C. albicans SA#1 whole filtrate antigen developed an antibody titer in the rabbits of 2,048 approximately 33 days after the initial injection and produced an antibody-antigen reaction with filtrates produced by other strains of *C. albicans*. The antiserum reacted with molecules in the filtrate Fractions II and III. Cellular antigens (obtained from sonicated whole cells) stimulated an antibody titer only to molecules greater than 10 K MW (Fraction III). Cell agglutination occurred with both types of antisera at a titer of 64.

Antiserum stimulated by the whole filtrate had a higher activity against the ethanol precipitates of the filtrate than with antiserum stimulated by cellular antigens and the high titer was reached in a shorter period of time. Cellular antigens required 12 weeks to develop a titer of 256 while the whole filtrate required only five weeks to develop a high titer of 2,048.

This study indicates that it is possible to significantly inhibit the growth of Sarcoma-180 in mice by using glycoprotein synthesized by a strain of *Canadida albicans*.

SUMMARY

The above experiments show highly significant results establishing that an ethanol precipitate of glycoprotein material synthesized by a strain of *Canadida albicans* was able to inhibit the growth of S-180 solid tumors in female Ha/ICR mice regardless of the method used to evaluate treatment effectiveness. Evaluation using mean tumor diameters indicated that all treatments were equally effective in decreasing tumor size. However, survival times indicated dose dependency; one double dose or two single doses produced significantly longer survival times than one single dose.

An important aspect of these experiments revealed the effect of the precipitate on the inhibition of the blood vessels supporting the growth of the Sarcoma 180 tumor primarily and the possible antibody-antigen reaction.

Ulcerations, hemorrhaging, or necrosis was not observed in the subcutaneous tissue surrounding the residual Sarcoma 180 tumor, and the ethanol precipitate was not toxic, lethal, or able to produce necrosis or hemorrhage at the injection site.

The filtrate, which contained the glycoprotein complex, stimulated the production of antibodies in rabbits within five weeks and the titer was greater than that obtained by using other immunogens. The antiserum produced precipitin lines against filtrates and agglutinated cells of other strains of Candida. Serum of mice treated only with the precipitate indicated maximal antibody-antigen reactions at the 6th and 7th days. Metabolic by-products in the chemically defined culture medium of several strains of *C. albicans were found to inhibit or stimulate their own cellular growth or that of other Candida strains.* carding the cells, precipitating the remaining filtrate with ethanol, and recovering the resulting glycoprotein of the precipitate.

2. The method of claim 1 wherein the step of precipitating the filtrate with ethanol is conducted with 95% ethanol.

3. The method of claim 1 wherein the chemical medium is composed of:
$CaCl_2.2H_2O$—0.1 g
NaCl—0.1 g
$MgSO_4.7H_2O$—0.4 g
$K_2HPO_4$—1.0 g
$(NH_4)_2SO_4$—3.5 g
glucose—40.0 g Table 1

The average tumor weight (g) and percent inhibition obtained from the experimental and control groups of mice after a single treatment of the glycoprotein by-products synthesized by *C. albicans* SA#1 in chemically defined medium.

| Day of treatment after transplant | Number of tumors per group of mice | Average tumor Weights (g) Wet $(W_e)^a$ | Dry $(W_e)$ | Percent tumor inhibition $W_e - W_c/W_c \times 100$ Wet | Dry |
|---|---|---|---|---|---|
| 3 | 7/10 | 64.7* | 13.8 | 29.70 | 34.59 |
| 4 | 5/10 | 85.8 | 22.4 | 6.74 | 6.16 |
| 5 | 6/10 | 75.8 | 21.4 | 17.60 | 1.42 |
| 6 | 2/10 | 23.9** | 6.1* | 74.02 | 71.10 |
| 7 | 6/11 | 20.8** | 4.9** | 77.40 | 76.80 |
| 8 | 9/10 | 53.6** | 14.7 | 41.74 | 30.30 |
| 9 | 3/10 | 11.0** | 2.2** | 88.04 | 89.60 |
| 10 | 2/9 | 17.9** | 4.8** | 80.54 | 77.25 |
| Control $(W_c)^b$ | 8/9 | 92.0 | 21.1 | | |

$^a W_e$ = Experimental Values.
*Chi-square values significant (p<0.01).
**Chi-Square values highly significant (p<0.001).
$^b W_c$ = Control Values.

Table 2

The average tumor weights (g) and percent inhibition obtained from the experimental and control groups of mice after multiple treatments of the glycoprotein by-products synthesized by *C. albicans* SA#1 in chemically defined medium.

| Days of treatment after transplant | Number of tumors per group of mice | Average tumor weights (g) Wet $(W_e)^a$ | Dry $(W_e)$ | Percent tumor inhibition $W_e - W_c/W_c \times 100$ Wet | Dry |
|---|---|---|---|---|---|
| Days 3 + 4 | 2/10 | 7.9** | 1.8* | 80.20 | 84.75 |
| Days 3,4, + 5 | 3/10 | 20.5* | 4.7 | 48.62 | 60.20 |
| Days 3,4,5, + 6 | 4/10 | 11.6** | 2.9* | 70.92 | 75.40 |
| Days 3,4,5,6, + 7 | 1/10 | 3.8** | 1.1* | 90.48 | 90.70 |
| Control $(W_c)^b$ | 7/7 | 39.9 | 11.8 | | |

$^a W_e$ = Experimental Values.
*Chi-square values significant (p 0.01).
**Chi-square values highly significant (p 0.001).
$^b W_c$ = Control values.

Table 3

Comparative analysis of surviving animals receiving varied treatments.

| | Number of animals | Survivors at evaluation day 55 | Percent survivors | Survivors without tumors | Median survival time (days) | Mean survival time (MST) (days) | Percent increase in MST from controls |
|---|---|---|---|---|---|---|---|
| Group 1 | 28 | 7 | 25 | 7 | 34.0 | 34.4 | 3.9 |
| 2 | 34 | 8 | 24 | 5 | 28.5 | 40.3 | 21.7 |
| 3 | 34 | 9 | 26 | 7 | 31.0 | 42.9 | 29.6 |
| 4 | 35 | 2 | 6 | 1 | 32.0 | 33.1 | |

Group 1 Treatment: one injection, 10 mg glycoprotein/ml on day 9.
2 Treatment: one injection, 20 mg glycoprotein/ml on day 9.
3 Treatment: two injections, 10 mg glycoprotein/ml on days 9 and 18.
4 Controls bearing S-180 tumor; no treatment.

I claim as my invention:

1. The method of making a Sarcoma 180 tumor growth inhibitor which comprises culturing *Candida albicans* SA#1 (CBS 5736) microorganism in a chemical medium containing glucose for about 30 days at about 30° C., centrifuging the resulting growth medium, discarding the cells, precipitating the remaining filtrate with ethanol, and recovering the resulting glycoprotein of the precipitate.

per liter of distilled water.

4. The method of claim 1 including the step of adding biotin to the medium.

5. The sarcoma 180 tumor growth inhibitor made by the method of claim 1.

* * * * *